(12) United States Patent
Brown et al.

(10) Patent No.: US 10,695,262 B2
(45) Date of Patent: Jun. 30, 2020

(54) FLEXIBLE VIBRATION MODULE FOR SNAP IN ATTACHMENT TO A GROMMET EMBEDDED IN A COMPRESSION WRAP

(71) Applicant: Brownmed, Inc., Boston, MA (US)

(72) Inventors: Ivan E. Brown, Marblehead, MA (US); Brandon Rodriguez, Westwood, MA (US); Daniel Joseph Breton, Boston, MA (US)

(73) Assignee: Brownmed, Inc., Boston, MA (US)

( * ) Notice: Subject to any disclaimer, the term of this patent is extended or adjusted under 35 U.S.C. 154(b) by 310 days.

(21) Appl. No.: 15/832,097

(22) Filed: Dec. 5, 2017

(65) Prior Publication Data

US 2019/0167516 A1 Jun. 6, 2019

(51) Int. Cl.
*A61H 23/02* (2006.01)
*A61H 9/00* (2006.01)
(Continued)

(52) U.S. Cl.
CPC ....... *A61H 23/02* (2013.01); *A61F 13/00051* (2013.01); *A61H 9/005* (2013.01); *A61H 23/006* (2013.01); *A61H 2023/0209* (2013.01); *A61H 2201/0153* (2013.01); *A61H 2201/0157* (2013.01); *A61H 2201/165* (2013.01); *A61H 2201/1645* (2013.01); *A61H 2201/5002* (2013.01); *A61H 2201/5023* (2013.01); *A61H 2205/06* (2013.01); *A61H 2205/062* (2013.01); *A61H 2205/081* (2013.01); *A61H 2205/102* (2013.01); *A61H 2205/12* (2013.01)

(58) Field of Classification Search
CPC .... A61H 23/02; A61H 23/00; A61H 23/0218; A61H 23/0236; A61H 2201/0157; A61H 2201/0175; A61H 2201/1645; A61H 2201/0153; A61H 7/001; Y10T 403/45; Y10T 403/453; Y10T 403/455; A61F 13/00051

See application file for complete search history.

(56) References Cited

U.S. PATENT DOCUMENTS 2,837,805 A * 6/1958 Larkin ...................... A41F 1/02
24/662
5,421,799 A * 6/1995 Rabin .................... A61H 7/006
2/410

(Continued)

FOREIGN PATENT DOCUMENTS

WO 2015101790 A1 7/2015
WO 2016051414 A4 4/2016

OTHER PUBLICATIONS

European Patent Office, extended European Search Report of Application 18210407.5, 9 pages, dated Apr. 4, 2019.

*Primary Examiner* — Justine R Yu
*Assistant Examiner* — Kelsey E Baller
(74) *Attorney, Agent, or Firm* — McKee, Voorhees & Sease, PLC (57) ABSTRACT

A flexible vibrating module with flexible radiating arms outwardly projecting around the module, with each arm having an associated coin motor which can optionally be operated at high frequency or low frequency or pulsing frequency, is shown in combination with a wrap having a snap in flexible grommet for the module to consistently orient properly the module with respect to a patient's muscles or joints.

20 Claims, 11 Drawing Sheets

(51) Int. Cl.
*A61F 13/00* (2006.01)
*A61H 23/00* (2006.01)

(56) References Cited

U.S. PATENT DOCUMENTS

| | | | | |
|---|---|---|---|---|
| 6,203,509 | B1 * | 3/2001 | Duboff | A61H 23/0263 |
| | | | | 601/138 |
| D520,144 | S * | 5/2006 | Cafaro | A61H 39/002 |
| | | | | D24/211 |
| 8,753,299 | B1 | 6/2014 | Waldon, Sr. | |
| 8,900,120 | B2 * | 12/2014 | Lewis | A61H 19/00 |
| | | | | 600/38 |
| 9,326,909 | B2 * | 5/2016 | Liu | A61H 23/00 |
| 9,775,769 | B2 | 10/2017 | Brown et al. | |
| 2005/0143679 | A1 * | 6/2005 | Gelber | A61H 7/005 |
| | | | | 601/15 |
| 2006/0041207 | A1 * | 2/2006 | Gross | A61H 23/02 |
| | | | | 601/15 |
| 2009/0171418 | A1 * | 7/2009 | Sarif | A61H 39/002 |
| | | | | 607/59 |
| 2012/0083721 | A1 * | 4/2012 | Karnwie-Tuah | A61H 23/02 |
| | | | | 601/46 |
| 2014/0066925 | A1 | 3/2014 | Howard | |
| 2014/0207219 | A1 * | 7/2014 | Dunbar | A61F 7/007 |
| | | | | 607/112 |
| 2014/0309563 | A1 * | 10/2014 | Park | A61H 23/02 |
| | | | | 601/21 |
| 2016/0008219 | A1 * | 1/2016 | Pollak | A61H 23/02 |
| | | | | 601/46 |
| 2016/0051439 | A1 | 2/2016 | Brown et al. | |
| 2016/0175187 | A1 * | 6/2016 | Leftly | A61H 23/02 |
| | | | | 601/46 |
| 2016/0302996 | A9 | 10/2016 | Leftly | |

\* cited by examiner

FLEXIBLE VIBRATION MODULE FOR SNAP IN ATTACHMENT TO A GROMMET EMBEDDED IN A COMPRESSION WRAP

FIELD OF THE INVENTION

This invention relates to a vibration pad or module and a compression wrap for releasable attachment to the pad. Both are designed for vibration therapy of muscles and joints afflicted with aching, soreness or injury.

BACKGROUND OF THE INVENTION

Both vibration therapy and compression wraps for muscles and joints have been around for some time, and both have been used with some degree of therapeutic success. While there are available massaging devices for muscles and joints, their success, or lack of it depend greatly upon their combined effectiveness, that is both the effectiveness of the wrap and the effectiveness of the vibration therapy. Each affects the other and collectively they affect the therapeutic success of the device/wrap in question.

With miniaturizing of vibration inducing modules the ability to be far more creative in developing vibration modules and wraps that affectively penetrate muscles and joints with vibrations and/or pulsations has increased tremendously. For examples of vibration wraps and or gloves, see the commonly owned and assigned U.S. Patent Brown et al. U.S. Pat. No. 9,775,769 issued Oct. 3, 2017, which is incorporated herein in its entirety by this reference. The Brown U.S. Patent '769 relates to particularly to an orthotic compression glove for massaging the fingers and digits. It uses coin motors with a rechargeable battery, with the unit embedded in a stretchable compression glove. For an example of a vibration knee wrap, one may look to Waldon U.S. Pat. No. 8,753,299 for massaging knees with a compression wrap that utilizes vibrating motors surrounding the kneecap.

Holding vibrating motors in a fixed location in a wrap regardless of the flexing of a joint to many different orientations offers some difficulty. That is to say, to enhance the vibration effectiveness the coin motors need to be juxtaposed closely to the muscle or joint in a correct orientation.

For the above reasons, some efforts have been made to produce vibration modules to flex with a moving joint for example of an athlete. In this regard see published PCT application, international publication number WO2016/051414A1, published Apr. 7, 2016. The corresponding publication, or more accurately corrected publication of the corresponding U.S. application is U.S. 2016/0302996, published Oct. 20, 2016. It relates to a wearable vibration device that employs a soft wearable module to deliver high energy vibration deep in the muscle and soft tissue when placed inside a liner. It is lined up with holes of an alignment wrap and straps with hook and loop fasteners are then tensioned to hold the wearable module against the skin. The problem is such units do not hold firmly and alignment can be jostled out of place, particularly by vigorous athletic motion.

With the developing coin motor technology and compression wrap technology there has been demonstration of a particular need for an improved flexible module or pad that will allow the pad to flexibly bend with the limb or joint to keep the vibrating motors tightly positioned against the wearer's skin, even in athletic movement.

Further there is a need for a unit which allows modification of the vibration frequency in a range of low to high and if deemed necessary even pulsed.

Further, there is a need for a vibration pad that can be attached to a compression wrap in a manner which assures that the orientation will constantly be the same when the two are combined together, thus providing assurance that proper and consistent orientation is achieved with each application of the wrap to a patient.

A primary objective of the present invention is to fulfill the above needs. Particularly the above mentioned specific needs are fulfilled by a unit having a bottom and top housing made of flexible polymer capable of translating vibration throughout the unit and from there directly to soft tissue or joints of a patient.

An important further feature addressed in the present invention is the arrangement of the array of motors arranged in a radial pattern surrounding the targeted pain area and the attachment technique involving a vibration pad pressed fit into a grommet secured to the wrap with the orientation of the grommet assuring that the vibration module is properly placed. It is therefore assured as secure and in a consistent and correct location.

SUMMARY OF THE INVENTION

This invention relates to a flexible vibration module that has the capability of adjustable vibration speed and if desired pulsating vibration with the unit being adapted for direct attachment to a flexible grommet that properly assures vibration pad positioning.

DETAILED DESCRIPTION OF THE PREFERRED EMBODIMENTS

The invention is generally shown in conjunction with FIGS. 1-6 as it relates to the particulars of construction of vibration pad or module 10. FIG. 7-14 demonstrate the wrap and flexible grommet that allows the vibration module 10 to be snapped into location within the wrap for assurance of proper position with respect to a wearer's muscles and/or joint.

The vibration module 10 is comprised of a housing 12 having an on/off switch 14, and a plurality of radiating flexible arms 16, 18, 20, 22, 24 and 26 that radiate outwardly from housing 12. In at least one embodiment, the flexible arms 16, 18, 20, 22, 24 and 26 are a silicone material capable of transferring vibrations. Terminal ends of arms 16, 18, 20, 22, 24 and 26 house coin motors 28, 30, 32, 34, 36 and 38 which are electrically connected by electrical wire connectors 40, 42, 44, 46, 48 and 50 to printed circuit board (PCB) 70, as is lithium battery 72 which also connects to electrical plug in 75 on printed circuit board 70. Mode switch 14 (push button on/off) allows the frequency to be varied from low to high frequency to vibration pulsing, depending on the number of times on/off switch 14 is pushed.

Figure 1:
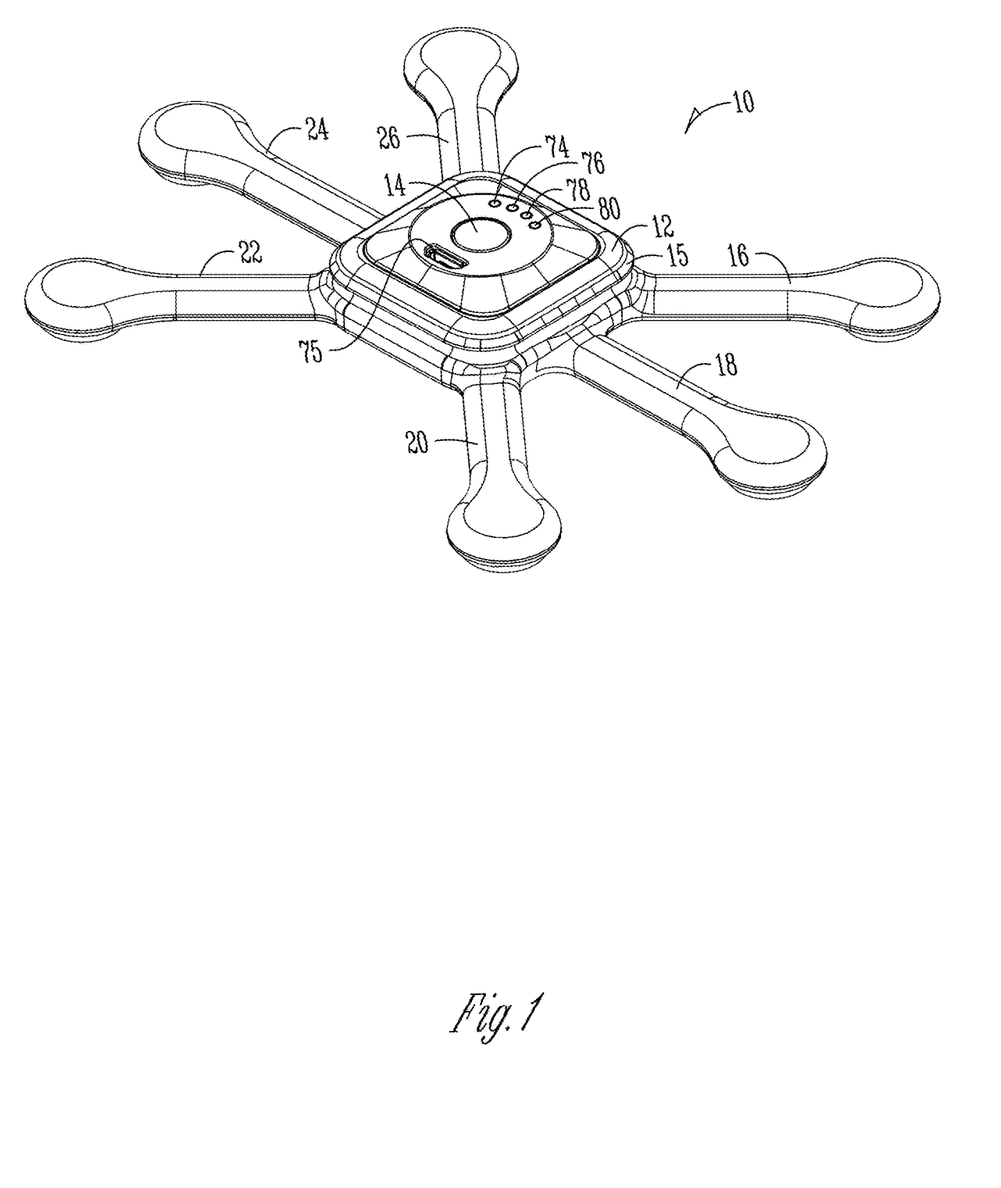
FIG. 1 is a top perspective view of the flexible vibration pad.
Figure 2:
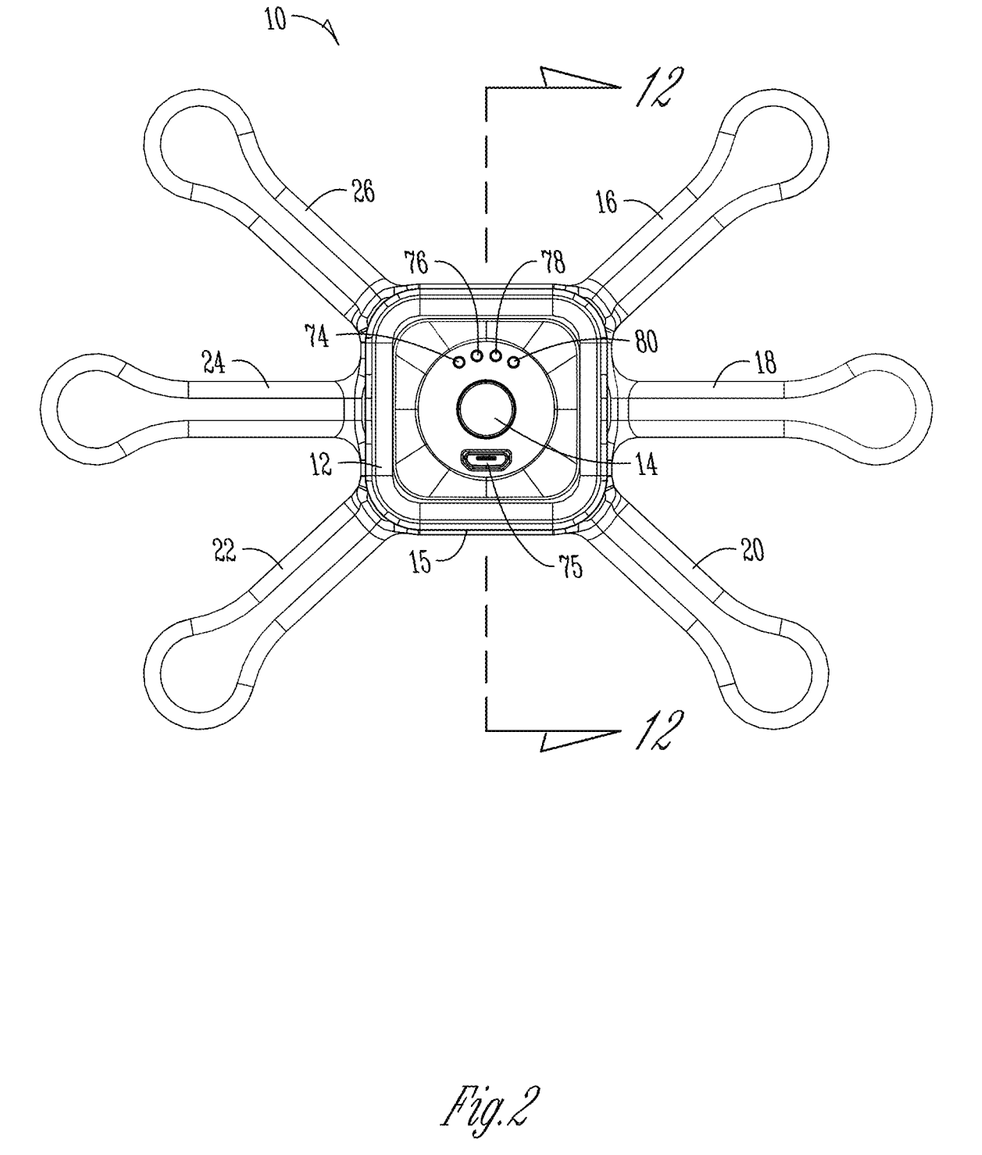
FIG. 2 is a plan view of the flexible vibration pad.

Vibrating coin motors are known and are available from a variety of sources. One example suitable for use herein are those described in our earlier U.S. Pat. No. 9,775,769A suitable supplier of those is Shenzhen Jingkefa Electronics Company Limited a battery suitable for the vibrating motors is lithium ion batteries such as a 3.7-volt lithium ion battery. Frequencies suitable for the vibration therapy are known and generally have been described as within the range of 20-50 Hz. A desired LED display as shown at 74, 76, 78, and 80 can also be housed within housing 12 used to indicate use mode and on/off.

Thus, to operate the unit one simply turns on the on/off switch 14 by pressing it, and then selects from the mode by how many pushes which is indicated by LED's 74, 76, 78, and 80.

The radiating arms of the vibration pad 16, 18, 20, 22, 24 and 26 are made of a flexible material, usually a polymeric material such as a silicon polymer. Housing 12 is made from thermoplastic elastomeric material, commonly referred to as TPE that is well known to those skilled in the art.

Figure 5:
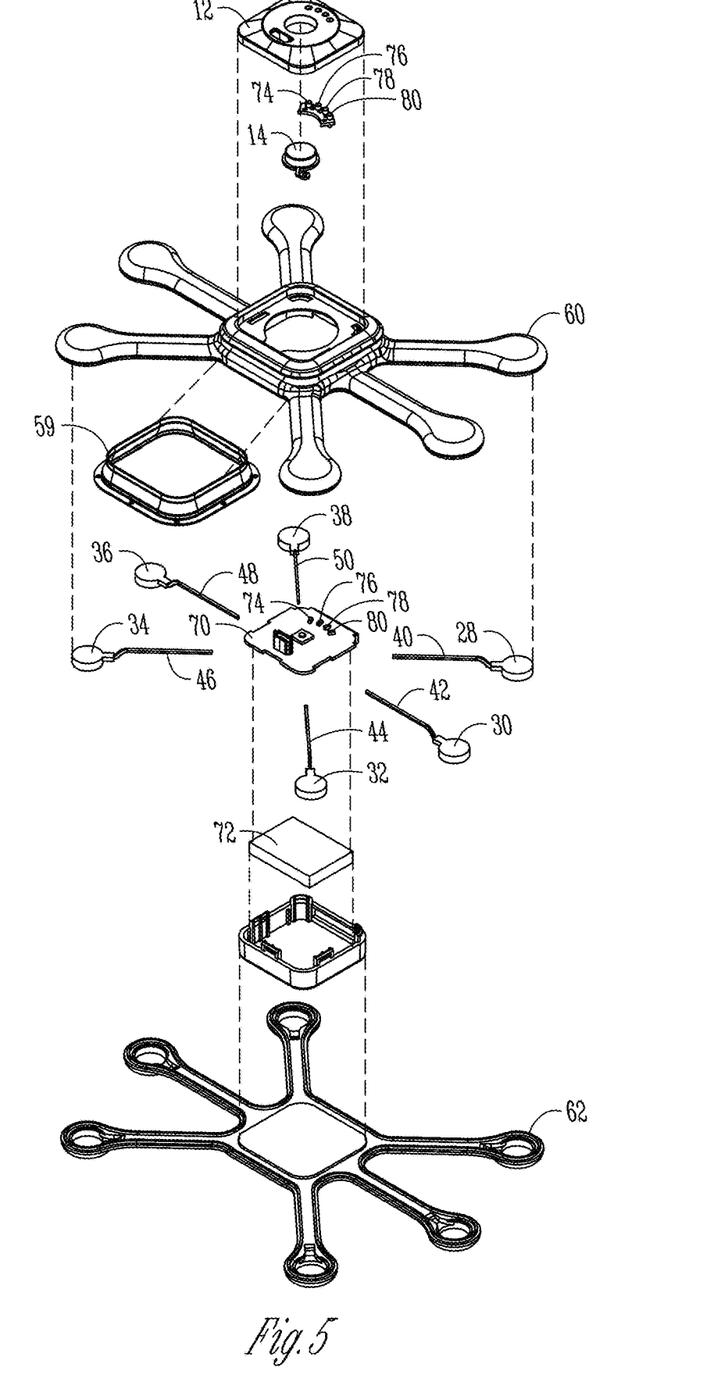
FIG. 5 shows an exploded view of the component parts of the flexible vibration pad from the top-down perspective.
Figure 6:
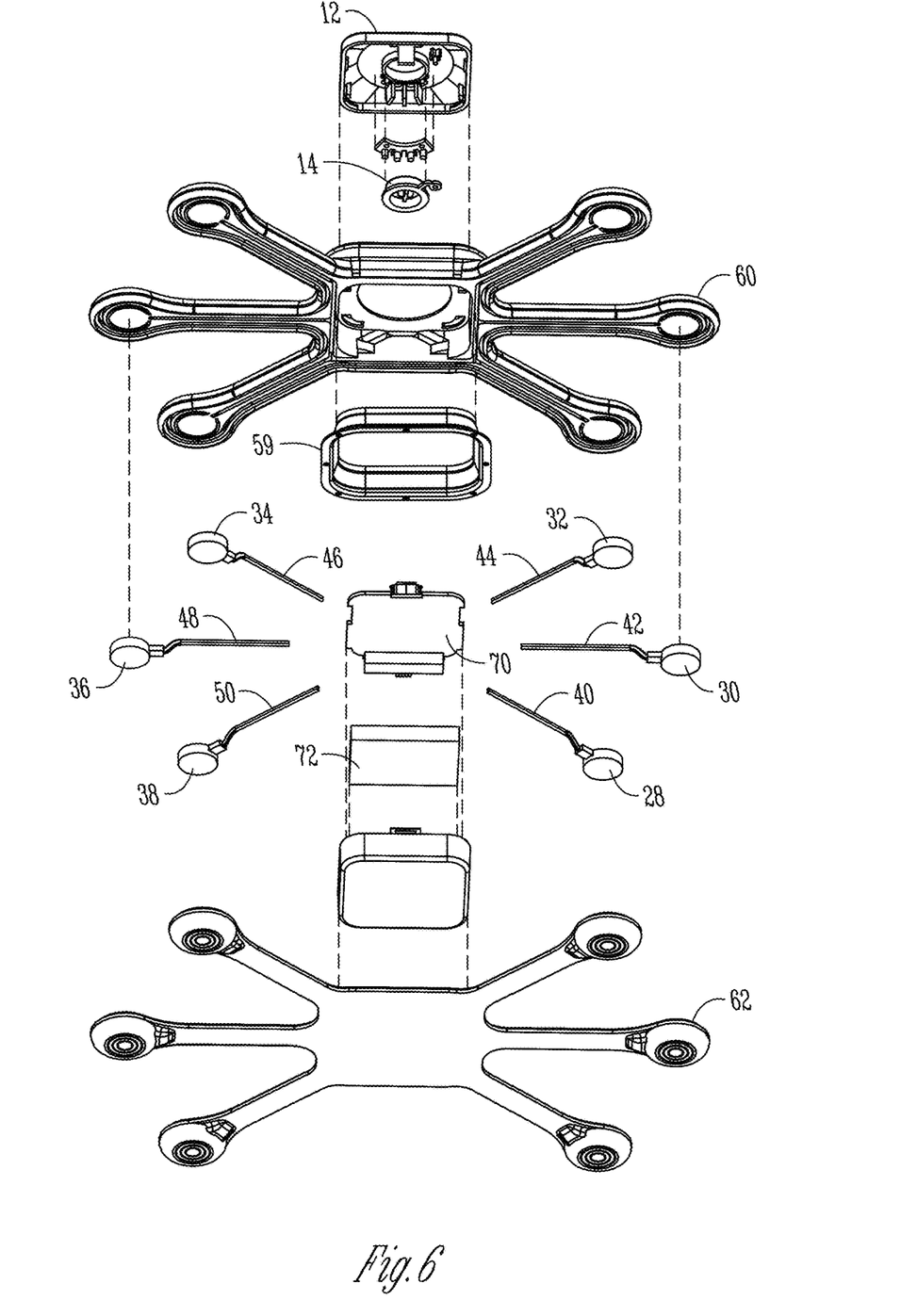
FIG. 6 shows another exploded view of the component parts of the flexible vibration pad from the bottom-up perspective.

As illustrated, the pad itself is preferably made of two parts of the same material a top 60 and a bottom 62 which are joined together at a midline seam to encapsulate the coin motors (28 to 38) and their electrical wire connectors (40 to 50).

The construction of the top cover 60 utilizes an over molding process to join the flexible silicone cover to a rigid internal frame 59. The internal frame 59 prevents migration or damage of the internally housed central electronics while also adding durability to the molded in FlexLOCK® channel. The use of over molding allows one to seamlessly integrate rigid material 59 into the pad design while still offering a comfortable and flexible one-piece top cover, 60.

Top cover 60 is created with dual hardness produced by a multi stage molding process allows a firm anchor for the interlocking channel and secure fit of PCB housing interface. Using a multi stage process allows us to control the hardness and flexibility in specific zones of the top housing. Arms of top cover consist of a lower hardness material 80-85 shore A hardness and gradually increases to 85-90 Shore A at the heart of pad, providing a semi-rigid core structure. The greater hardness provides structure and shape memory to the flexible pad 10. Hard material acts as an isolator that reflects the vibration down towards user's extremity. Hard top cover 60 houses and protects the internal PCB 70 and battery, 72.

Bottom cover 62 is lesser hardness or 70-72 Shore A hardness. The thin walls maximize vibration and flexibility. Soft material with raised surfaces grip to user's extremity and maximizes the translation of vibration to user. The thin walls also allow us to maximize the energy produced by the coin motor in an efficient draw that produces the desired run time 40-45 minutes with a small compact 3.4v power supply.

Module assembly uses a silicone compatible adhesive coupled with molded interlocking channels to allow for a sanitary sealed channel without the need for additional hardware or assembly. The use of flexible silicone compatible adhesive and molded channels allows for durable assembly without loss in flexibility from additional hardware or fasteners.

Figure 11:
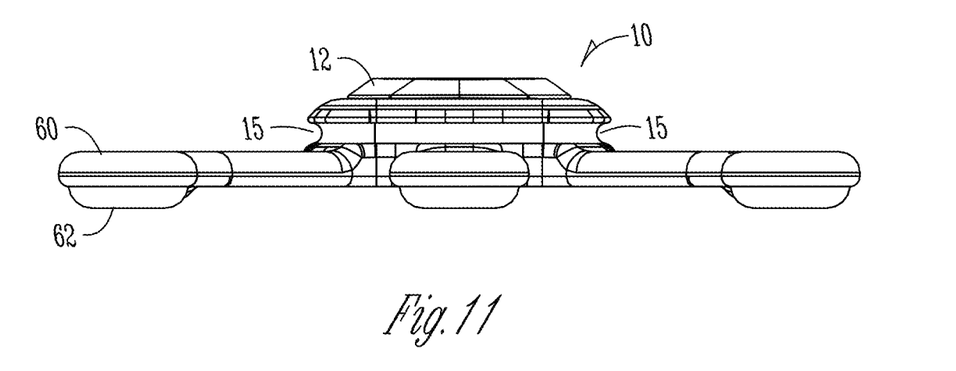
FIG. 11 is a side view of the flexible vibration pad clicked in the grommet of the wrap.
Figure 12:
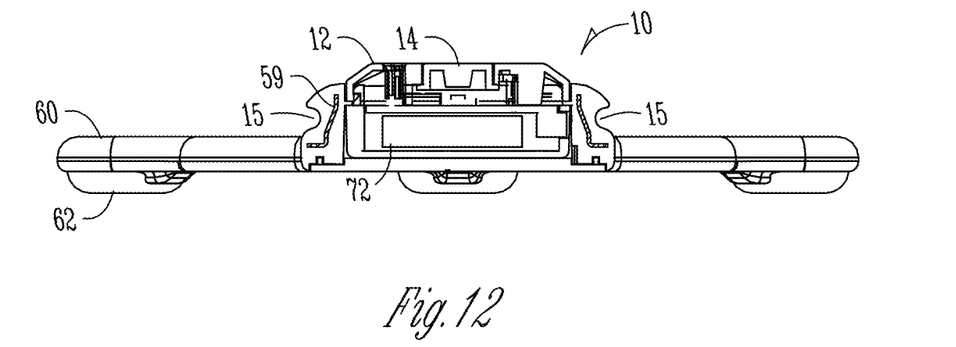
FIG. 12 shows a cross sectional view of FIG. 2 along line 12-12 of FIG. 2.
Figure 13:
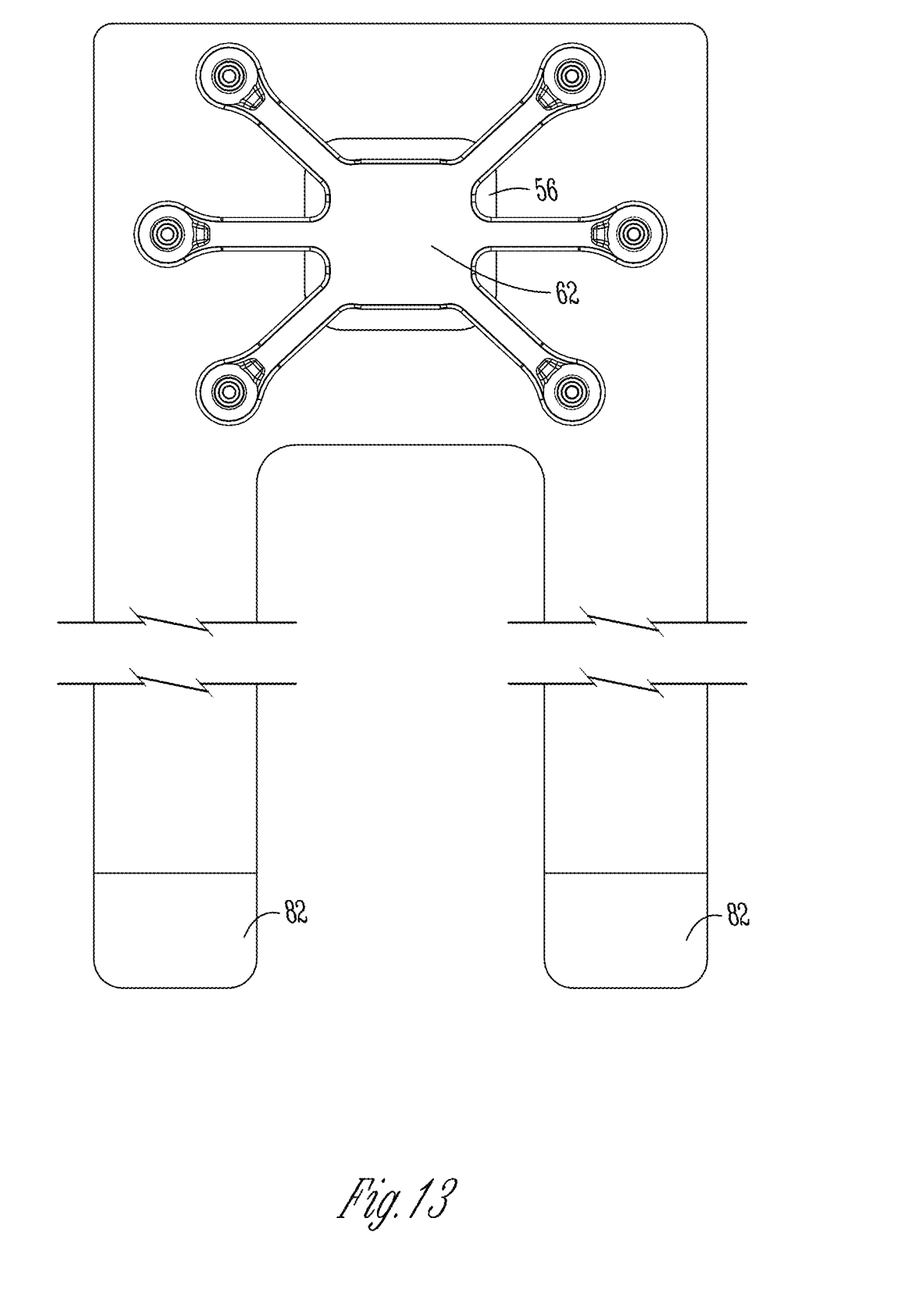
FIG. 13 shows a bottom view of the arm wrap of FIG. 7 with the flexible vibration pad clicked in the grommet of the arm wrap of FIG. 7.
Figure 14:
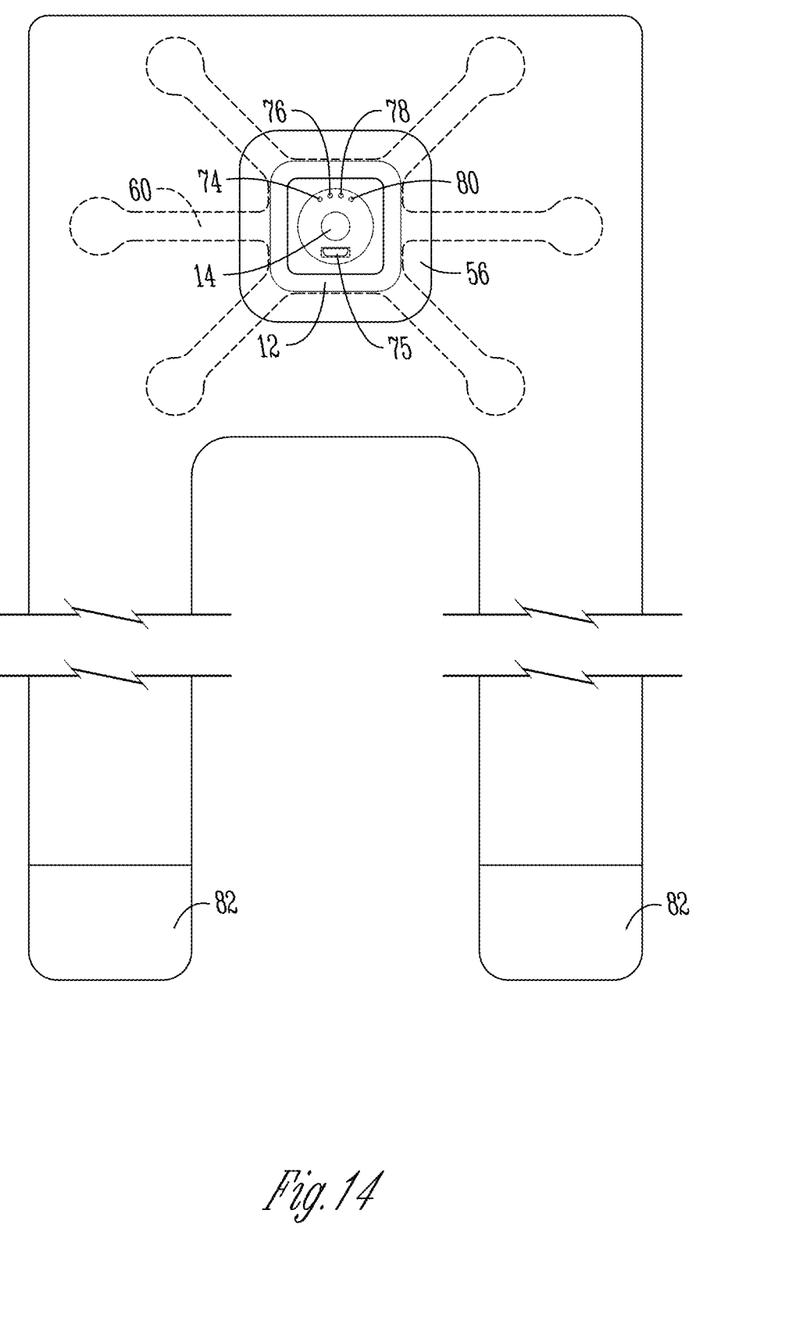
FIG. 14 shows a top view of the arm wrap of FIG. 7 with the pad clicked in the grommet of the shin wrap.

As earlier described, this combination of the flexible vibration module 10 and wraps may be used with a variety of differing wraps, many referred to as compression wraps. It can be used in combination for example with a knee wrap, an elbow wrap, a calf or shin wrap, an ankle or foot wrap, upper thigh wraps, lower back wraps, wrist wraps, and shoulder wraps. The wrap is a non-limiting feature as long as it has the snap in grommet as for example illustrated in FIGS. 7-14. The flexible grommet 56 is particularly shown in a snapped in relationship with the vibration module 10 in FIG. 11 and in cross section through the housing in FIG. 12. FIG. 13 illustrates the inside or skin side of the vibration module bottom and snapped in relationship ready for wrapping. FIG. 14 illustrates the top side with only the housing 12 top showing; the interior part is in dotted line relationship for the flexible arm 16, 18, 20, 22, 24, and 26 as lead line 80 demonstrates. As is illustrated in FIG. 11 the housing 12 has rim 15 which snaps into the grommet holding the module in place. Because flexible grommet 56 has flexible edges or skirt 57, it also can be snapped out by simply pushing back. However, it must be held correctly in the desirable orientation position by the snap-in snap-out relation with top of housing 12 of the vibration module 10.

The flexible grommet 56 click-in system consists of a molded channel in the top housing of the vibration module 15 that will lock into the flexible silicone grommet skirt 57. The flexible grommet 56 can be sewn or bonded to a wide variety of fabrics and allows the vibration module to seamlessly integrate into braces, wraps, and clothing. The grommet itself, 56 is highly flexible and capable of flexing and stretching to form around virtually any part of the body without effecting fit or comfort. The "press to lock" system allows the vibration module to be quickly and easily moved to different wraps or parts of the body. The FlexLOCK grommet 56 holds vibration module 10 securely in place during fitting and placement ensuring that the user can easily apply the pad to the treatment area and also prevents migration during use. The FlexLOCK grommet 56 also utilizes a pass-through open face allowing access to the PCB 70 interface and charging port during treatment. Users can easily identify mode and battery life as well as make adjustments without the need to remove the unit.

Figure 7:
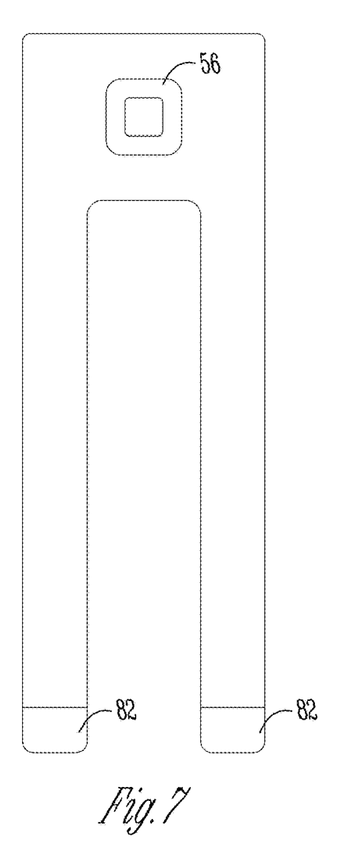
FIG. 7 shows an arm wrap top view with a click-in grommet.
Figure 8:
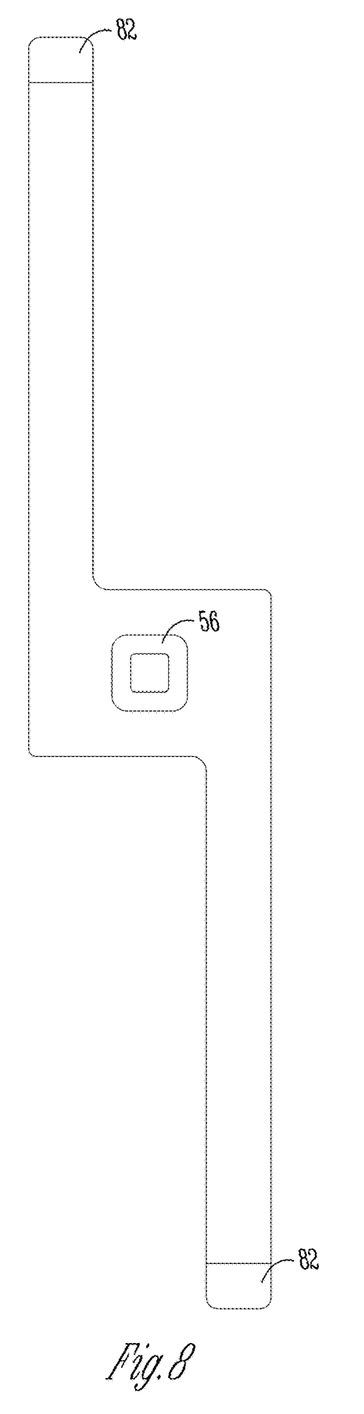
FIG. 8 shows a knee wrap top view with a click-in grommet.
Figure 9:
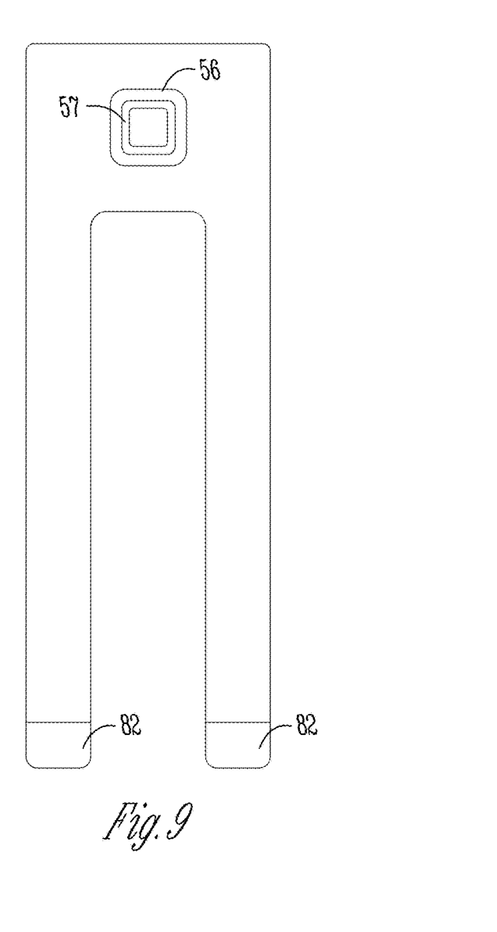
FIG. 9 shows the bottom view of arm wrap of FIG. 7.
Figure 10:
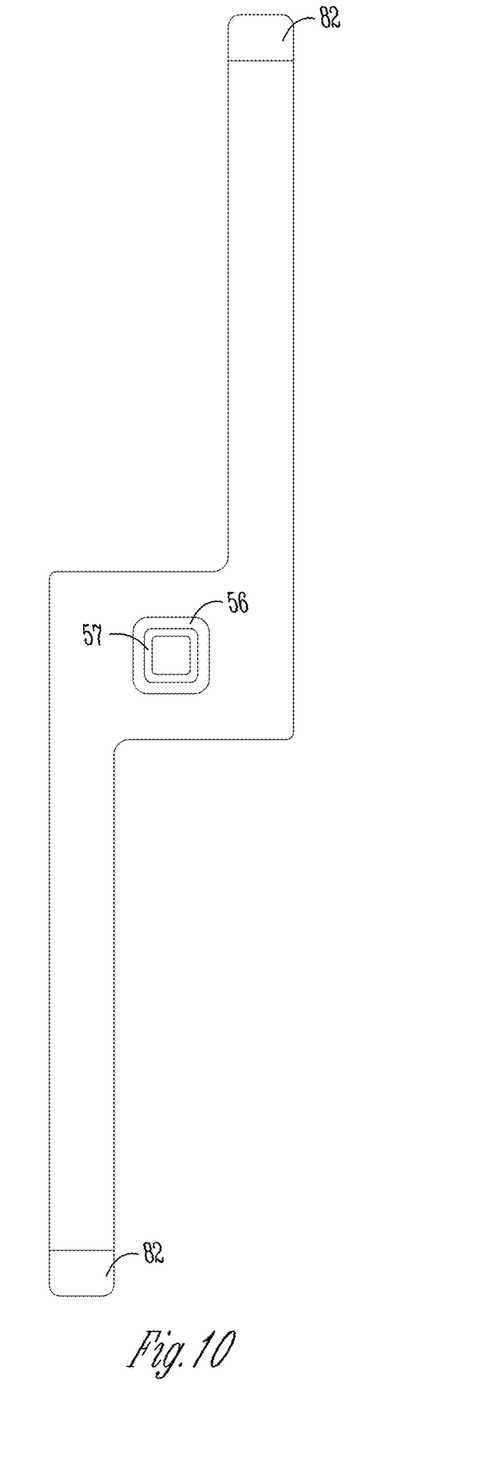
FIG. 10 shows the bottom view of the knee wrap of FIG. 8.

As illustrated at the ends of the wraps FIGS. 7 and 8 are typical hook and loop fasteners 82 used to secure the wrap in place on a patient's limb.

In the actual operation the unit works as follows. Operation module 10, or more accurately the top of its housing 12 is pushed through flexible grommet 56 and snapped into place in skirt 57 so that it is removably secured to the wrap for example 52 arm wrap and 54 knee wrap. The wrap is then place on the limb at the desired location with the straps wrapped around and hooked tightly. On/off button 14 is pushed and one of the mode switches 74, 76, 78 selected and vibration begins. Battery 72 is recharged as needed by a recharge receptacle 75.

Figure 3:
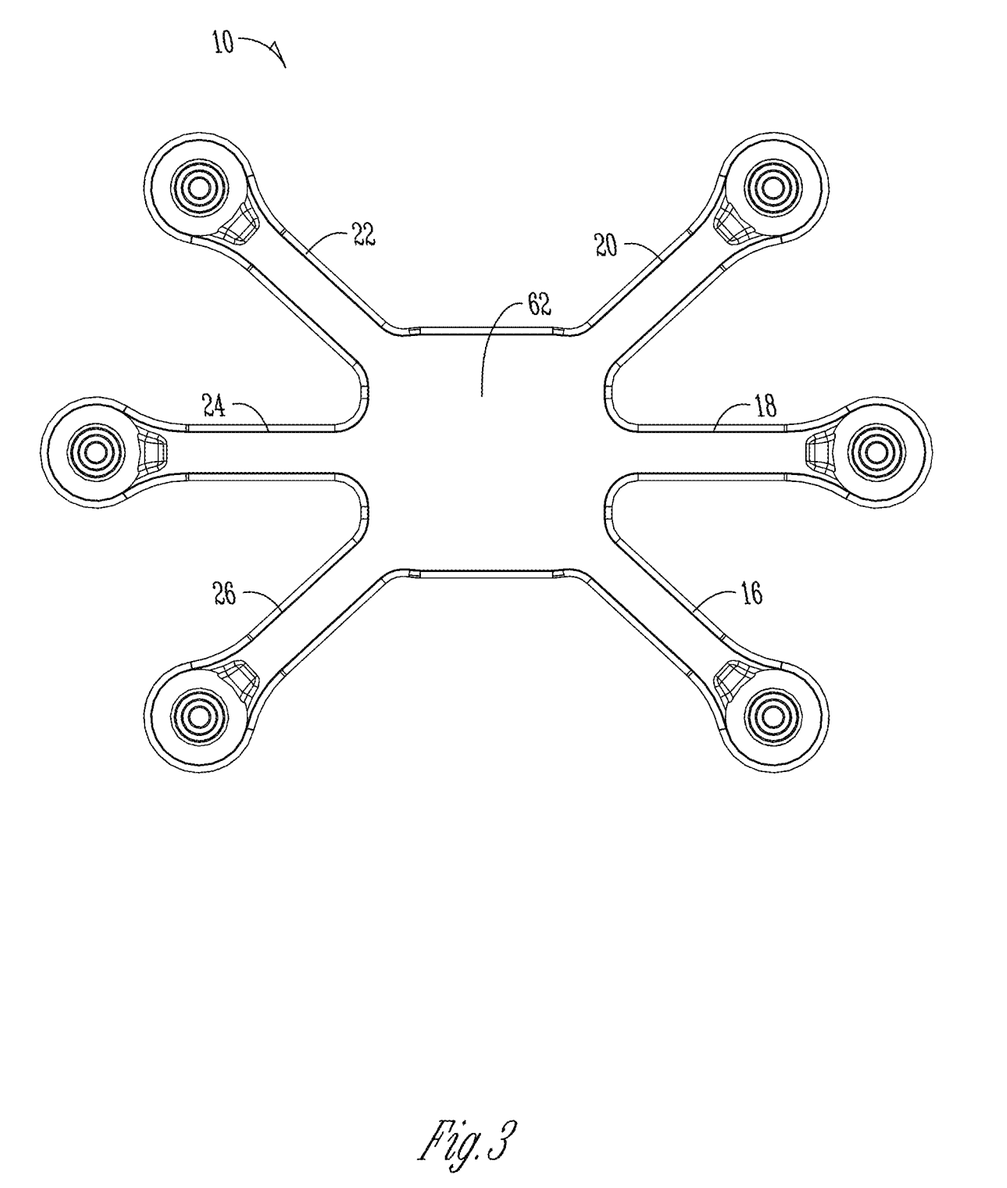
FIG. 3 is a bottom view of the flexible vibration pad.
Figure 4:
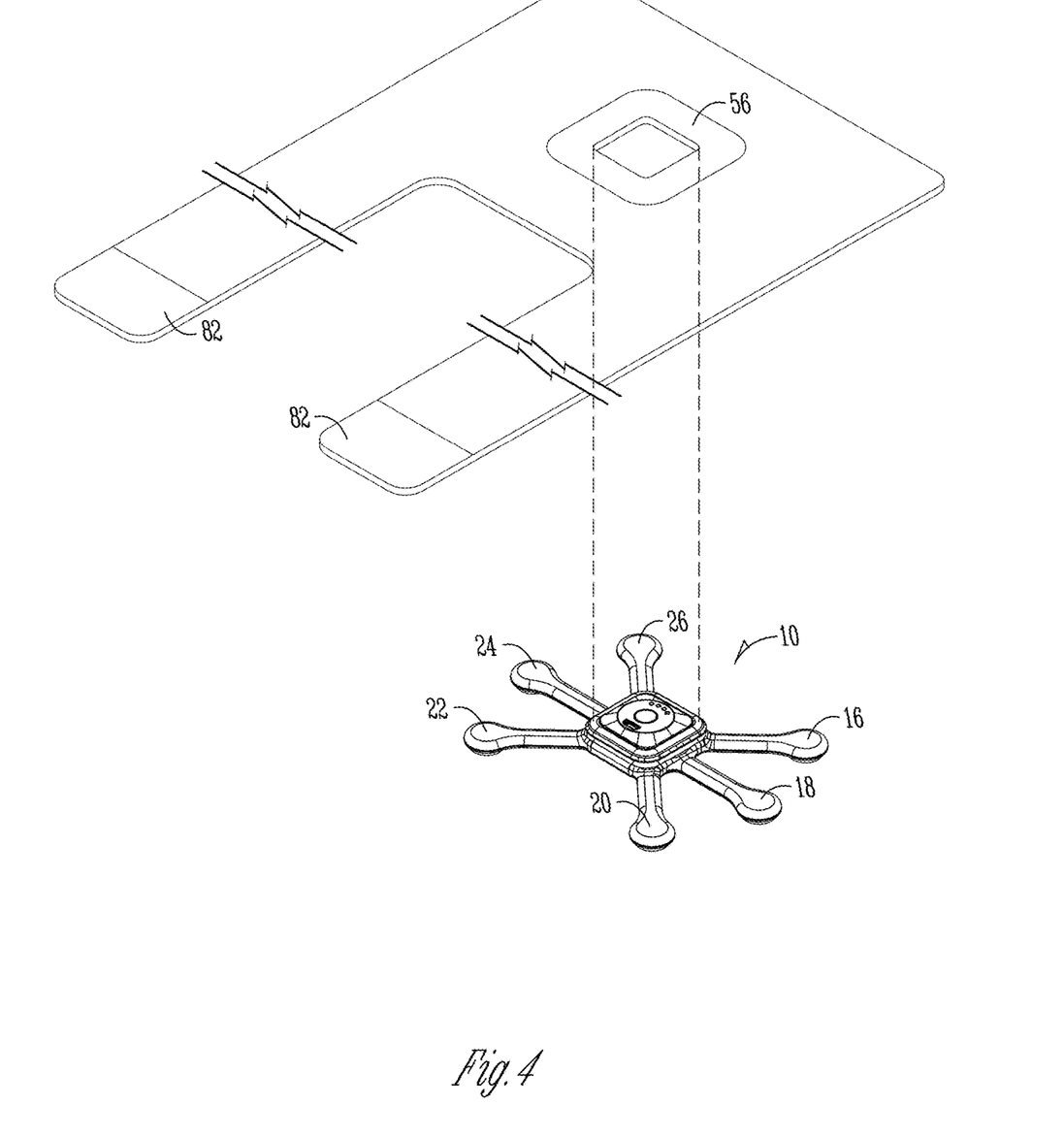
FIG. 4 shows an exploded view of how the flexible vibration pad may click into the grommet of a shin wrap.

As best shown in FIGS. 3 and 6 the bottom of the vibration pad 62 exterior surface is textured to assist in place holding against the skin of a patient.

The unit is held securely and cannot rotate freely or move out of position because of the removable but secure holding of grommet 56. It therefore can be seen that the invention accomplishes at least all of its stated objectives.

What is claimed is:

1. A vibration wrap, comprising:
   a vibration module having a housing,
   a rechargeable battery with an on/off switch in said housing,
   a plurality of flexible arms radiating outwardly from said housing,
   each arm of said plurality of flexible arms terminating in a coin motor which is electrically connected to said rechargeable battery;
   a compression joint wrap with a grommet;
   said grommet comprising a silicone polymer grommet skirt, and wherein the vibration module further includes a molded channel, said molded channel supported by a rigid frame of the housing and capable of locking into the silicone polymer grommet skirt and being adapted to allow said housing to be removably secured to said compression joint wrap.

2. The vibration wrap of claim 1 wherein the compression joint wrap is selected from the group consisting of gloves, forearm wraps, upper arm wraps, shoulder wraps, thigh wraps, shin wraps, calf wraps, knee wraps, ankle wraps and lower back wraps.

3. The vibration wrap of claim 2 wherein the on/off switch has a high frequency vibration setting, a low vibration frequency setting and a pulsing setting.

4. The vibration wrap of claim 1 wherein said plurality of flexible arms comprise a silicone material capable of transferring vibrations.

5. The vibration wrap of claim 1 wherein the grommet is sewn into said compression joint wrap.

6. The vibration wrap of claim 1 wherein the coin motors are embedded in the flexible arms, and further wherein the flexible arms have a bottom, textured surface.

7. The vibration wrap of claim 1 wherein the vibration module is comprised of a top portion and a bottom portion joined to create a sealed unit.

8. The vibration wrap of claim 7 wherein the top portion comprises a flexible silicone polymer.

9. The vibration wrap of claim 8 wherein the bottom portion comprises a thermoplastic elastomer.

10. The vibration wrap of claim 1 wherein the plurality of flexible arms comprise six flexible arms.

11. A vibration pad and a grommet on a compression joint wrap, comprising:
    a vibration module having a housing;
    said housing comprising a fastener, an internal, rigid frame, and a flexible cover over molded onto the internal, rigid frame;
    a rechargeable battery with an on/off switch in said housing;
    a plurality of flexible arms radiating outwardly from said housing; and
    each arm of said plurality of flexible arms terminating in a coin motor which is electrically connected to said rechargeable battery;
    said grommet comprising a silicone polymer grommet skirt, and the vibration module further includes a molded channel, said molded channel supported by a rigid frame of the housing and capable of locking into the silicone polymer grommet skirt and being adapted to allow said housing to be removably secured to said compression joint wrap.

12. The vibration pad and the grommet on the compression joint wrap of claim 11 wherein said rechargeable battery is a lithium ion battery.

13. The vibration pad and the grommet on the compression joint wrap of claim 12 wherein said housing includes a printed circuit board, electrically connected to said lithium ion battery and said coin motors.

14. The vibration pad and the grommet on the compression joint wrap of claim 11 wherein said flexible cover has an upper or top pad portion and a bottom pad portion which are fixed together to cover said coin motors, said rechargeable battery, and a printed circuit board.

15. The vibration pad and the grommet on the compression joint wrap of claim 11 wherein the on/off switch has a high frequency vibration setting, a low vibration frequency setting, and a pulsing setting.

16. The vibration pad and the grommet on the compression joint wrap of claim 11 wherein said plurality of flexible arms comprise a silicone material capable of transferring vibrations.

17. The vibration pad and the grommet on the compression joint wrap of claim 11 wherein the coin motors are embedded in the flexible arms, and further wherein the flexible arms have a bottom textured surface.

18. The vibration pad and the grommet on the compression joint wrap of claim 14 wherein the upper or top pad portion comprises a flexible silicone polymer.

19. The vibration pad and the grommet on the compression joint wrap of claim 14 wherein the bottom pad portion comprises a thermoplastic elastomer.

20. The vibration pad and the grommet on the compression joint wrap of claim 11 wherein the plurality of flexible arms comprise six flexible arms.

* * * * *